US008069245B2

(12) United States Patent
Bolle et al.

(10) Patent No.: US 8,069,245 B2
(45) Date of Patent: Nov. 29, 2011

(54) METHOD AND COMPUTER NETWORK FOR OPERATION OF MEDICAL TECHNICAL COMPUTER APPLICATIONS AT RESPECTIVE NETWORKED COMPUTERS

(75) Inventors: Nikolaus Bolle, Baiersdorf (DE); Thies Theisen, Nürnberg (DE)

(73) Assignee: Siemens Aktiengesellschaft, Munich (DE)

( * ) Notice: Subject to any disclaimer, the term of this patent is extended or adjusted under 35 U.S.C. 154(b) by 139 days.

(21) Appl. No.: 11/761,553

(22) Filed: Jun. 12, 2007

(65) Prior Publication Data

US 2008/0005333 A1    Jan. 3, 2008

(30) Foreign Application Priority Data

Jun. 12, 2006    (DE) .......................... 10 2006 027 222

(51) Int. Cl.
*G06F 15/173*    (2006.01)
*G06F 15/16*    (2006.01)
(52) U.S. Cl. .......................... 709/226; 709/225; 709/229
(58) Field of Classification Search .................. 370/463, 370/468; 705/1, 8; 707/8, 9, 10, 104.1, 200, 707/201; 709/203, 216, 224, 225, 226, 240, 709/244, 229; 726/6, 18, 26; 710/39, 40, 710/41
See application file for complete search history.

(56) References Cited

U.S. PATENT DOCUMENTS

| 4,961,224 | A   | * | 10/1990 | Yung ................................ 726/4 |
| 5,530,903 | A   | * | 6/1996  | Calvignac et al. ............... 710/41 |
| 5,842,173 | A   | * | 11/1998 | Strum et al. ...................... 705/1 |
| 6,411,218 | B1  | * | 6/2002  | Johnson ......................... 710/107 |
| 6,795,830 | B1  | * | 9/2004  | Banerjee et al. ............... 707/200 |
| 7,149,779 | B2  | * | 12/2006 | Bocionek ....................... 709/206 |
| 2003/0026226 | A1 | * | 2/2003 | Miura ........................... 370/335 |
| 2004/0015602 | A1 | * | 1/2004 | Goldhammer et al. ........ 709/235 |
| 2004/0042489 | A1 | * | 3/2004 | Messick et al. ............... 370/468 |
| 2004/0192322 | A1 | * | 9/2004 | Dacosta et al. ............ 455/452.1 |
| 2006/0140205 | A1 | * | 6/2006 | Baik et al. ..................... 370/412 |

FOREIGN PATENT DOCUMENTS

WO    WO 2004006520 A1 *    1/2004

* cited by examiner

*Primary Examiner* — Joshua Joo
*Assistant Examiner* — Jonathan Willis
(74) *Attorney, Agent, or Firm* — Schiff Hardin LLP

(57) ABSTRACT

In a method for operation of medical-technical computer applications in a computer network with a central computer and a number of peripheral computers, the central computer allocates resources among the respective peripheral computers for usage of the computer applications. For this purpose, a priority level is associated with each of the peripheral computers and/or the users of the peripheral computers. The central computer then provides the individual peripheral computers with the specific resources in an allocation that is dependent on their associated priority level. A computer network has a central computer and a number of peripheral computers and implements the foregoing.

8 Claims, 3 Drawing Sheets

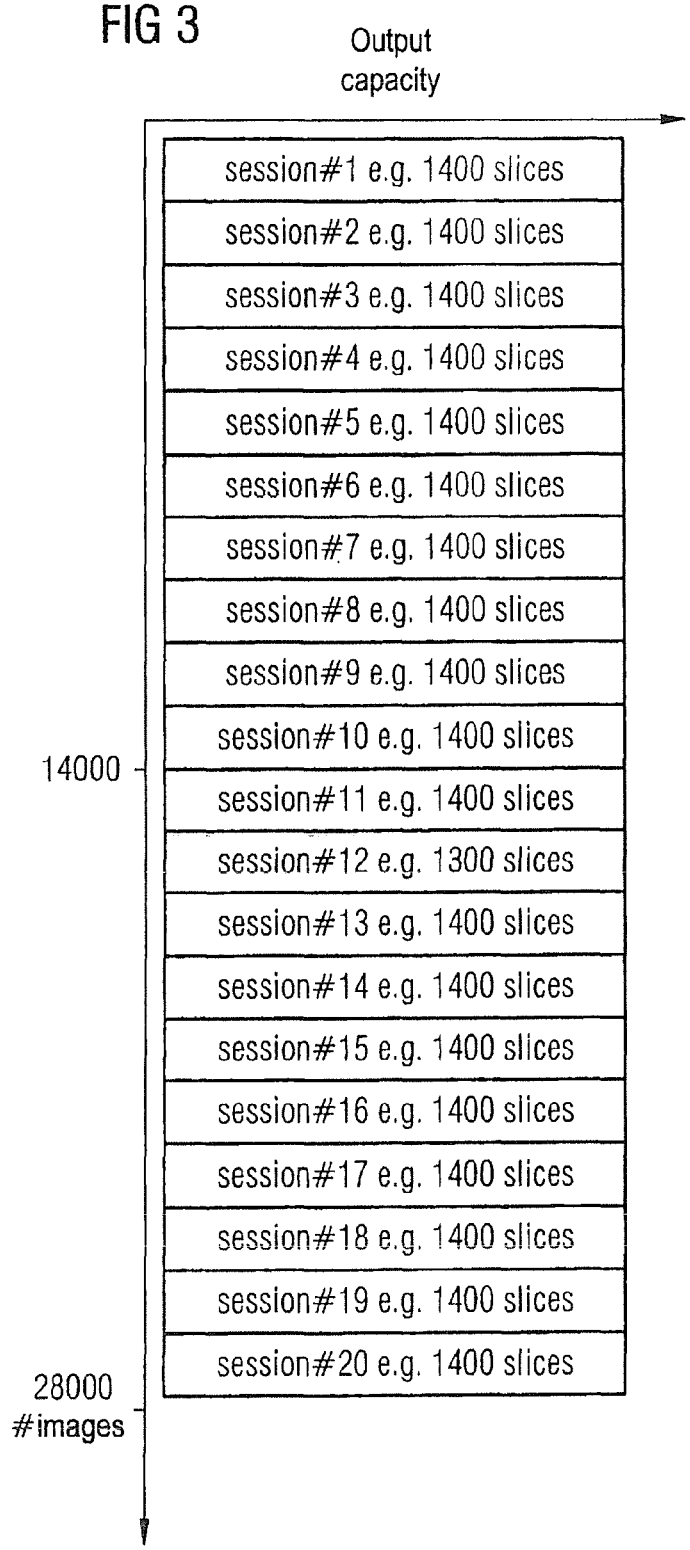

METHOD AND COMPUTER NETWORK FOR OPERATION OF MEDICAL TECHNICAL COMPUTER APPLICATIONS AT RESPECTIVE NETWORKED COMPUTERS

BACKGROUND OF THE INVENTION

1. Field of the Invention

The present invention concerns a method and a computer network for operation of medical-technical computer applications in the network.

2. Description of the Prior Art

The operation of medical-technical computer applications in a computer network requires that particular attention be directed to the installation sites of the computer. As used herein "computer application or computer applications" means applications that can be utilized by a peripheral computer, for example programs for controlling apparatuses, for observation and evaluation of images, for information acquisition etc. In contrast to computer networks for use in administration operations, or by financial service providers, or by production operations or agencies, medical-technical computer applications are used in hospitals, medical practices or emergency clinics. In that context, an error-free and time-saving functioning of the medical-technical computer application is essential because human lives may be at stake. This necessity in medial technical computer applications outweighs the economical utilization of a computer application that may be more important in a different operation context.

Various installation sites are possible for medical-technical computer applications such as, for example, an emergency ward of a hospital in which work is conducted under the highest time pressure and highest concentration. Installation sites within a hospital are also possible at which reaction speeds are of subordinate importance. Such installation sites are, for example, an archive or a library of the same hospital. In an emergency ward, seconds or minutes can decide between life and death of a just-admitted patient. In the library, by contrast, a longer wait time is of lesser importance. For example, a nurse's station or a chief physician's console also differ in terms of their importance as installation sites for a computer or a computer application in a hospital. A chief physician requires a medical-technical computer application, possibly for assessment of a just-admitted, critically ill patient; a nurse at the nurse's station checks the medication of a patient at his or her station with the same computer application. The different importance is apparent.

SUMMARY OF THE INVENTION

It is an object of the present invention to provide a solution to the aforementioned problem and to ensure a safe and fast operation of medical-technical computer applications in sensitive areas, in particular in emergencies.

This object is achieved by a method according to the invention for operation of medical-technical computer applications in a computer network with a central computer and a number of peripheral computers, wherein the central computer provides the peripheral computers with specific resources for usage of the computer applications, and wherein a priority level is associated with the various peripheral computers and/or the various users of the peripheral computers. The central computer then provides the individual peripheral computers with the specific resources dependent on the priority level associated with them.

The term "central computer" as used herein means a computer (for example a server) that takes on administration tasks in the network and rations out resources to other computers. The term "peripheral computer" (or "client") as used herein means any workstation or other computer that accesses resources allocated by the central computer. For example, in a network with a number of central computers, a computer can serve as a central computer with regard to certain applications and as a peripheral computer with regard to other applications.

The allocated resources can be, for example, storage space in the working memory of the central computer and/or each individual peripheral computer, or a data transfer rate or data transfer capacity between the central computer and the individual peripheral computers. Another example of the provided resources can be the permission (enablement) to use a particular computer program installed on the computer network. For some applications (for example for special, expensive applications for evaluation or assessment of magnetic resonance or computer tomography slice images) only a limited number of parallel users is allowable.

For specific computer applications that exhibit an intensive graphics, the graphics card of the peripheral computer or of a central computer (in particular the total number of simultaneously loaded images) can also be a limiting resource. The further graphics capacities or images to be presented is thus also a resource to be provided that can be monitored (controlled) through the inventive method.

The allocation of priority levels in accordance with the invention allows specific peripheral computers and/or users to be preferentially supplied with resources for specific applications within the computer network. For example, it can be ensured that peripheral computers that, due to their location (for example in an emergency ward), typically must employ full capacity for all necessary applications, are not inhibited by other activities on the computer network. A corresponding user priority can be granted to specific users, possibly only temporarily for the duration of an emergency service.

In addition to a central computer, a computer network in accordance with the invention has a number of peripheral computers that are coupled into a common network and are configured to operate with a data exchange among one another. A priority level determination unit that determines a priority level for each peripheral computer and/or user of the peripheral computer is connected in the computer network, for example at or in the central computer. The association of the priority level with the individual peripheral computers and/or users advantageously ensues according to specific criteria that can be predetermined by a user authorized for this purpose, for example a system administration. Furthermore, a resource allocation device that associates specific resources with the individual peripheral computers according to their associated priority level is connected in the computer network, for example at or in the central computer.

According to the invention, a current priority level is associated with each peripheral computer while it is operating and active on the computer network. In an embodiment, a hierarchy (ranking) of the peripheral computers and/or users that are active at a current point in time is established, corresponding to these priority levels. According to this hierarchy, the central computer can provide the specific resources to the individual peripheral computers without having to check and compare the individual priority levels upon every resource allocation. The hierarchy is updated, for example, when a peripheral computer is added to the network or exits the network or when a user logs on or off. For this purpose, the computer network has a hierarchy unit (for example at or in the central computer) that organizes the individual peripheral computers relative to one another according to their priority levels.

In typical computer networks a unique identifier is normally associated with each individual peripheral computer. The peripheral computer can be therewith identified at any time relative to the central computer. For this purpose, for example, the central computer can include an identification device that is configured to identify the peripheral computer relative to the central computer using the identifier. A priority level can then be associated with the individual identifiers, for example in a table. The current priority level thus is known in the computer network by each peripheral computer at all times. This is particularly advantageous when the hierarchy of the subsequently active peripheral computer is updated by the deactivation or an activation of a further peripheral computer.

A unique user identifier can also be assigned to each user in order to identify the users relative to the central computer. A previously assigned priority level can likewise also be determined in a simple manner for every individual user by means of the user identifiers.

Combining the unique computer identifier with the unique user identifier by means of a predetermined or predeterminable algorithm enables the allocation of a priority level dependent on the result of this combination. For example, a particularly high priority level can be associated with a specific user as long as he works at a specific peripheral computer.

Storage space in the computer network, in particular hard drive storage space, working memory space or graphics memory space as well as the data transfer capacity in the network, in particular between the central computer and the individual peripheral computers, can be among the resources to be allocated. Furthermore, the CPU computational capacity of the central computer and/or a maximum number of applications of a predeterminable application type that can be used in parallel can be among the allocated resources.

An advantage of the inventive method is that not only the respective individual resources but also a combination of the individual resources can be allocated to the individual peripheral computers and/or users according to the principle of the inventive method.

In an embodiment of the method, a specific priority level is associated with a specific group of peripheral computers. This can be arbitrarily many peripheral computers and is not limited to a specific number. This eases the administration of the priority levels of the peripheral computers by a system administrator within the method according to the aforementioned principle. For example, a particularly high priority level can be associated overall with all peripheral computers in the emergency ward.

In most cases a higher proportion of resources is simply provided to a peripheral computer/user with higher priority level. This means that peripheral computers/users with a low priority level are also adequately operated for their tasks, even though they are not operated with the same performance as the peripheral computer/user with the higher priority levels. Under specific conditions, for example when the resources are severely limited and peripheral computers/users with particularly high priority level require specific resources to unusual degrees, peripheral computers/users with a low priority level may no longer be operated at all for a specific time span. For example, given a state in which a maximum allowable number of peripheral computers is reached, in an embodiment of the method specific resources are made available to a further peripheral computer only when an active peripheral computer with a lower priority level is active. The resources are then taken from said peripheral computer with a lower priority level and are allocated to the further peripheral computer.

DESCRIPTION OF THE DRAWINGS

FIG. 3 is an application example of the inventive method for a graphic-intensive computer application.

DESCRIPTION OF THE PREFERRED EMBODIMENTS

Figure 1:
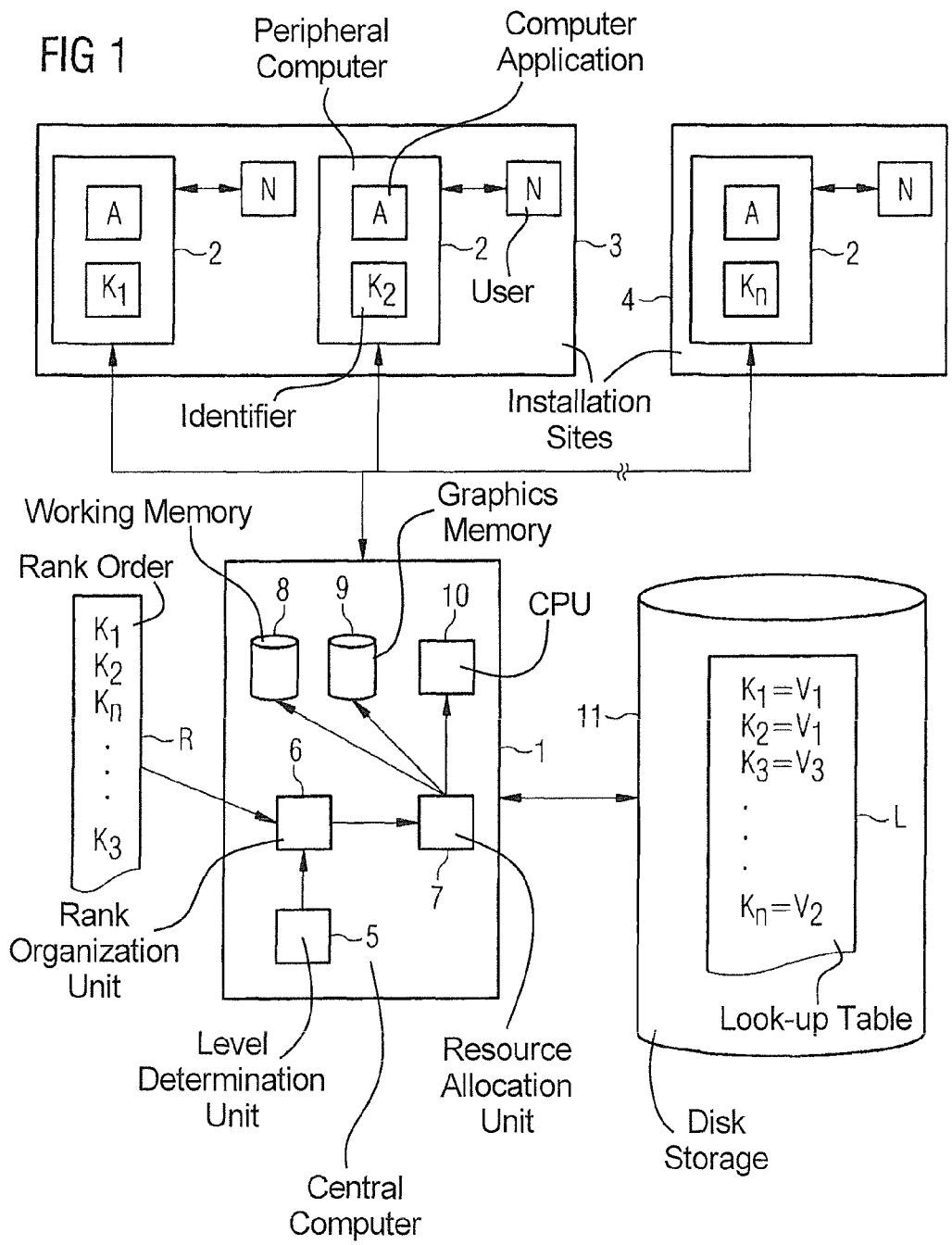
FIG. 1 is a schematic representation of a computer network constructed and operating in accordance with the invention.

The example of a computer network schematically represented in FIG. 1 is a network that is installed in a hospital. The network has a central computer 1 that is connected with a number of peripheral computers 2 (clients) at various installation sites 3, 4.

The central computer 1 is, for example, a server. This is generally clearly more powerful than each individual peripheral computer 2, however, but individual peripheral computers 2 divide the capacity of the central computer 1. This is especially the case when individual peripheral computers 2 access data via the network for specific computer applications A that are executed at the peripheral computers 2, thereby accessing storage space or accessing computing capacity of the central computer 1. The applications A can (as shown here) directly run on the peripheral computers 2 and from there access specific resources (such as, for example, a databank) at the central computer 1 that are required for the application. In principle, however, the actual application can run directly on the central computer 1, with only front ends, which provide the user interface for the application, being installed on the individual peripheral computers 2. This difference is not normally recognizable to the actual user.

Each peripheral computer 2 has a unique identifier $K_1, K_2, K_3, \ldots K_n$. Each peripheral computer 2 can be uniquely identified in the computer network with this identifier $K_1, K_2, K_3, \ldots K_n$. Furthermore, a priority level $V_1, V_2, V_3$ is associated with each peripheral computer 2. The priority level $V_1, V_2, V_3$ of the appertaining peripheral computer 2 is here selected dependent on the installation site 3, 4 of the peripheral computer 2. Peripheral computers 2 at installation sites 3 receive a high priority level $V_1$, peripheral computers 2 at installation sites 4 with lower priority (for example in an archive) receive a lower priority level $V_3$.

For this purpose, the central computer 1 has a priority level determination unit 5 that determines the associated priority level $V_1, V_2, V_3$ for the individual peripheral computer 2 according to its identification. For example, for this purpose the determination unit 5 can have or access a look-up table L that contains all identifiers $K_1, K_2, K_3, \ldots K_n$ with the associated priority levels $V_1, V_2, V_3$. The association in the look-up table L can be modified, for example, by a system administrator. Here the look-up table L is stored in a disk storage 11 of the central computer 1.

Each peripheral computer 2 is used by a user N. Every user N is likewise unambiguously identifiable in the computer network by his or her own user identifier. A priority level can also be associated with the user N. Through an algorithm (not shown in FIG. 1), the priority level of the peripheral computer can be combined with the priority level of the user N into an overall priority level. For example, a mathematical multiplication of the priority levels can be implemented or an average value of the priority levels can be formed as a possible algorithm for combination of the priority level $V_1$, $V_2$, $V_3$ of the peripheral computer 2 with the priority level of the user N.

Thus it is possible to assign a very high priority level V to a peripheral computer 2 in an emergency ward of a hospital and to assign a very low priority level V3 to a peripheral computer 2 in a hospital archive. If a user N with higher priority level (for example a physician in emergency services) uses the peripheral computer 2 with low priority level V3, his priority level has an influence on the total priority level that raises the total priority level. This is primarily advantageous when users N of peripheral computers 2 are active at changing installation sites 3, 4.

For simplification of the resource administration, all peripheral computers 2 operating in the computer network are sorted in a rank order R by a rank organization unit 6, corresponding to their priority levels $V_1$, $V_2$, $V_3$. If multiple peripheral computers 2 have the same level among priority levels $V_1$, $V_2$, $V_3$, the organization in the rank order can depend on the priority level of the current user. The resources are assigned to the individual peripheral computers 2 according to this rank order R. This can be controlled by a resource allocation unit 7 of the central computer 1.

The priority level determination unit 5, the rank association unit 6 and the resource allocation unit 7 can be realized as software modules of the central computer 1.

Among other things, the computation time of a CPU 10 of the central computer 1 as well as storage space in a working memory 8, in a graphics memory 9, or in a disk storage 11 of the central computer 1, are among the resources that can be allotted to the peripheral computer 2.

A further example of resources that are provided in limited scope and, for this reason, are particularly advantageously allotted according to assigned priority levels $V_1$, $V_2$, $V_3$, are licenses for computer applications A. If the computer network of the hospital owns, for example, ten licenses for a specific computer application, it is thus normally ensured that this computer application can only be simultaneously used ten times at maximum.

The method according to the described principle is particularly suited to ensure such a licensed application can always be utilized quickly in an emergency. Using the rank order R it can be ensured that the ten peripheral computers 2 that are highest in the rank order R can start and execute the application A at any time.

If the application A is thus called at a peripheral computer 2, it can only execute said application A when:
 (1) Ten peripheral computers have not already loaded the computer application A, or
 (2) at least one of the ten peripheral computers has a lower priority level or stands lower in the rank order.

The peripheral computer 2 with the lower priority level is then forced to and exit the computer application A. The appertaining user is informed of the priority situation and the application is shut down in a proper manner at this application and the current state is saved so that the user, upon recall of the application, can begin with the state in which the application was interrupted.

Figure 2:
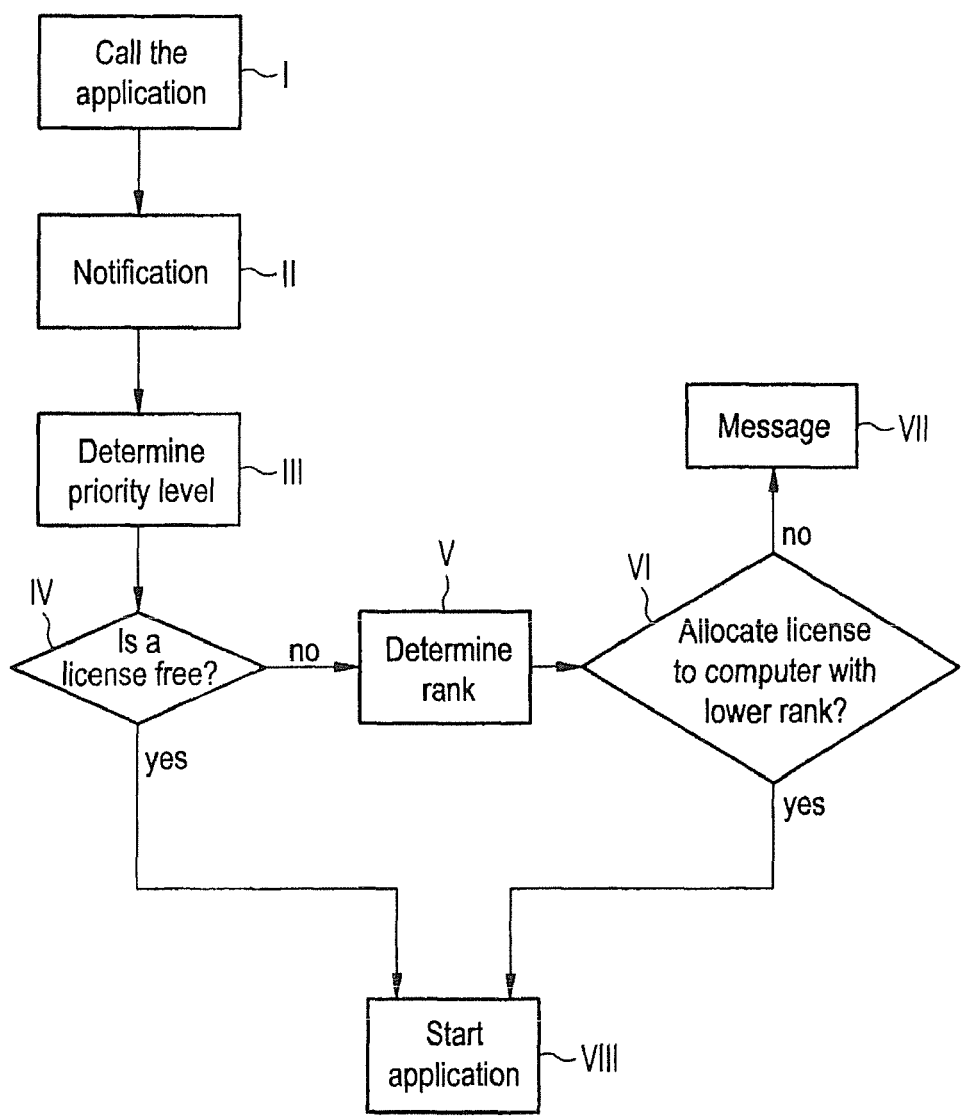
FIG. 2 is a flowchart scheme for resource allocation in accordance with the invention.

The flowchart of FIG. 2 shows an exemplary embodiment of such a ranking, wherein a further peripheral computer 2 calls a specific computer application in a computer network. This computer application is a limited resource in the computer network since it is limited to a specific number of parallel usages. Like the other peripheral computers 2 which are already using the computer application A, the further peripheral computer 2 also has a priority level.

The computer A is called at the peripheral computer 2 in step I. After the notification of the peripheral computer 2 at the central control computer 1 for usage of the computer application in step II, the determination of the priority level of the peripheral computer 2 ensues in step III.

If the priority level is determined, in step IV a check ensues as to whether a license for the appertaining application is free. If this is the case, an allocation of resources immediately ensues in step VIII, meaning that the peripheral computer 2 can use the application.

By contrast, if too many other peripheral computers 2 are already working with this application such that all licenses are exhausted, the rank of the peripheral computer in the rank order R is established in step V. In step VI it is then checked whether the other peripheral computers 2 stand higher in the rank order R. If all previous peripheral computers 2 stand higher in the rank order R, no resources are provided to the further peripheral computer 2, meaning that the computer application A cannot be started and the user N receives a message about this result in step VII.

If at least one peripheral computer 2 that possesses a lower priority level is located among the peripheral computers 2 working until now with the computer application A, an allocation of resources ensues in step VIII, meaning that the peripheral computer 2 can use the application. The application is then ended or interrupted as described above on the peripheral computer 2 of lower rank.

FIG. 3 symbolizes a resource allocation in the form of memory space in a graphics card for a medical-technical computer application, for example, software for making a medical finding. Only a limited number of images (here a maximum of 28,000 images) can be loaded simultaneously. These resources are divided such that a maximum of 1400 computed tomography images can be loaded by twenty applications running in parallel. A further peripheral computer 2 that must load 5000 further computed tomography images nevertheless can operate with the inventive method in the event that the peripheral computer 2 and/or the user N logged in at the peripheral computer 2 has a higher priority level than one of the previous twenty peripheral computers 2 or the respective users thereof. In order to be able to load all 5000 computed tomography images, however, the peripheral computer/user must have a higher priority level than four of the previous peripheral computers/users. Since a peripheral computer 2 in an installation area 3 of high priority (such as, for example, an emergency ward) should have a very high priority level (generally the highest priority level), normally the 5000 required computed tomography images can be loaded immediately at this peripheral computer 2.

The method workflow as well as the shown computer network and its components are only exemplary embodiments that can be modified in various ways by those skilled in the art without departing from the scope of the invention. In particular a number of different priority levels (i.e. a high priority level for a first application, but a low priority level for a different application) can also be associated with a peripheral computer 2 for various applications.

We claim as our invention:

1. A method for operating medical-technical computer applications at respective computers networked in a computer network, said computers comprising a central computer and a plurality of peripheral computers, comprising the steps of:
 for each peripheral computer, assigning a computer priority level thereto that is associated with the peripheral computer itself;

for each user of each of said peripheral computers, assigning a user priority level thereto that is associated with said each user;

defining a predetermined condition that, when satisfied, requires a temporary allocation of resources among the peripheral computers for executing respective medical technical computer applications at the peripheral computers;

when said predetermined condition is satisfied, in said central computer, automatically assigning, to each of said peripheral computers, a temporary current rank dependent on a current configuration of said computer network according to which of said users is currently using which of said peripheral computers, said central computer calculating respective current ranks for each of said peripheral computers by a mathematical operation involving the computer priority level associated with a respective peripheral computer and the user priority level associated with the current user of the respective peripheral computer, said temporary current rank being assigned to each peripheral computer only while the current user is logged into the respective peripheral computer and being updated for each peripheral computer when the current user logs out of the respective peripheral computer; and from said central computer, allocating, via the network, said resources among the peripheral computers for executing said respective medical-technical computer applications at the peripheral computers, dependent on the temporary current ranks associated with the peripheral computers for a time during which said predetermined condition is satisfied.

2. The method as claimed in claim 1 comprising assigning a unique identifier to each of said peripheral computers that identifies each said peripheral computer to the central computer, and associating the respective priority levels with the respective unique identifiers of the peripheral computers.

3. The method as claimed in claim 1 comprising assigning a unique user identifier to each user of a peripheral computer that identifies said each user to the central computer, and assigning said priority level to the individual user identifiers.

4. The method as claimed in claim 1 comprising allocating resources among said peripheral computers selected from the group consisting of storage space, data transfer capacity in the network, CPU capacity of the central computer, and a maximum number of medical-technical applications available for use in parallel.

5. The method as claimed in claim 1 comprising assigning a priority level to a predetermined group of said peripheral computers.

6. The method as claimed in claim 1 comprising allocating a higher proportion of said resources to said peripheral computers having a higher priority level.

7. The method as claimed in claim 1 wherein said network has a maximum allowable number of peripheral computers connectable thereto and, in a state of said network in which said maximum allowable number is reached, allocating resources from said central computer to a further peripheral computer only when resources are being provided by the central computer to an active peripheral computer having a lower priority level than said further peripheral computer, and said central computer thereupon taking said resources from the active peripheral computer with a lower priority level and allocating those resources to said further peripheral computer.

8. A computer network comprising:

a central computer and a plurality of peripheral computers networked with said central computer by a computer network;

a priority level determination unit that associates a computer priority level with at least one of each individual peripheral computer and a user priority level with each user of said peripheral computers;

said central computer being configured to receive a designation that a predetermined condition exists that requires a temporary allocation of resources among the peripheral computers for executing respective medical-technical computer applications at the peripheral computers, and said central computer being configured to automatically assign, when said predetermined conditions exist to each of said peripheral computers, a temporary current rank dependent on a current configuration of said computer network according to which of said users is currently using which of said peripheral computers, said central computer calculating respective current ranks for each of said peripheral computers as a mathematical combination of the computer priority level associated with a respective peripheral computer and the user priority level associated with the current user of the respective peripheral computer, said temporary current rank being assigned to each peripheral computer only while the current user is logged into the respective peripheral computer and being updated for each peripheral computer when the current user logs out of the respective peripheral computer; and a resource allocation unit associated with said central computer configured to allocate said resources among the peripheral computers for executing said medical-technical applications at the peripheral computers according to the temporary current ranks associated with the peripheral computers for a time during which said predetermined conditions exist condition exists.

* * * * *